(12) United States Patent
Santaniello et al.

(10) Patent No.: US 10,524,948 B2
(45) Date of Patent: Jan. 7, 2020

(54) MICRO-ADJUSTABLE TELESCOPING ARMS FOR ORTHOPEDIC BRACES

(71) Applicant: CORFLEX, INC., Manchester, NH (US)

(72) Inventors: Steven Santaniello, Cranston, RI (US); Benjamin Glace, Dunbarton, NH (US)

(73) Assignee: ORTHOCARE MEDICAL EQUIPMENT, LLC, Manchester, NH (US)

( * ) Notice: Subject to any disclaimer, the term of this patent is extended or adjusted under 35 U.S.C. 154(b) by 793 days.

(21) Appl. No.: 14/161,132

(22) Filed: Jan. 22, 2014

(65) Prior Publication Data

US 2014/0207038 A1    Jul. 24, 2014

Related U.S. Application Data

(60) Provisional application No. 61/755,114, filed on Jan. 22, 2013.

(51) Int. Cl.
*A61F 5/01* (2006.01)

(52) U.S. Cl.
CPC .......... *A61F 5/0102* (2013.01); *A61F 5/0125* (2013.01)

(58) Field of Classification Search
CPC ........ A61F 5/01; A61F 5/0102; A61F 5/0125; A61F 2005/0167; A61F 2005/0158; A61H 2201/165; A61D 9/00; B29L 2031/7532
USPC ..... 602/5, 6, 16, 23, 26; 128/845, 882, 892; 601/33, 34, 35, 29
See application file for complete search history.

(56) References Cited

U.S. PATENT DOCUMENTS

| 3,389,481 | A | * | 6/1968 | England | A43B 3/26 36/97 |
| 4,817,588 | A |   | 4/1989 | Bledsoe | |
| 4,825,852 | A | * | 5/1989 | Genovese | A61H 1/0259 482/901 |
| 4,886,054 | A |   | 12/1989 | Castillo et al. | |

(Continued)

FOREIGN PATENT DOCUMENTS

| EP | 0139689 B1 | 8/1985 |
| EP | 1086672 A2 | 3/2001 |

OTHER PUBLICATIONS

U.S. Appl. No. 14/169,582, filed Jan. 31, 2014, Pending.

(Continued)

*Primary Examiner* — Anna K Kinsaul
*Assistant Examiner* — Caitlin A Carreiro
(74) *Attorney, Agent, or Firm* — Davis & Bujold PLLC; Kimberly A. W. Peaslee

(57) ABSTRACT

An adjustable orthopedic strut system with a locking system that utilizes an incremental or "micro" adjustment method that is size adaptable and easy to use. The adjustable orthopedic strut system has a locking system, adjustable support members, struts, and an indented molded track. The adjustable orthopedic strut system improves user fitting and sizing creating better support and comfort. The adjustable orthopedic strut system provides "micro" incremental adjustments on support members to allow strategic positioning of the support members near surgical incisions. Furthermore, the adjustable orthopedic strut system locks and telescopes on a non-interrupted strut surface with minimal "snag" points, thus reducing the difficulty in achieving fine adjustments.

9 Claims, 6 Drawing Sheets

(56) References Cited

U.S. PATENT DOCUMENTS

| | | |
|---|---|---|
| 5,443,444 A | 8/1995 | Pruyssers |
| 5,472,410 A | 12/1995 | Hamersly |
| 5,653,680 A | 8/1997 | Cruz |
| 5,745,963 A | 5/1998 | Graziano |
| 5,887,318 A | 3/1999 | Nicoletti |
| 5,890,435 A | 4/1999 | Thoman et al. |
| 5,975,557 A | 11/1999 | Snoke et al. |
| 6,390,492 B1 | 5/2002 | Bumgarner et al. |
| 6,527,733 B1 | 3/2003 | Ceriani et al. |
| 6,821,261 B2 * | 11/2004 | Doty ................ A61F 5/0123 128/882 |
| 7,189,212 B2 | 3/2007 | Popp et al. |
| 7,384,406 B2 | 6/2008 | Enzerink et al. |
| 7,399,288 B2 | 7/2008 | Chao |
| 7,758,648 B2 | 7/2010 | Castleman et al. |
| 7,806,844 B2 | 10/2010 | Outred et al. |
| 7,833,181 B2 | 11/2010 | Cormier et al. |
| 8,048,013 B2 | 11/2011 | Ingumundarson et al. |
| 8,123,709 B2 | 2/2012 | DeHarde et al. |
| 8,425,439 B1 | 4/2013 | McKeon et al. |
| 2006/0155230 A1 | 7/2006 | Mason et al. |
| 2008/0188784 A1 | 8/2008 | Ceriani et al. |
| 2010/0130899 A1 | 5/2010 | Chao |
| 2010/0262052 A1 | 10/2010 | Lunau et al. |
| 2011/0009786 A1 | 1/2011 | Chan |
| 2011/0082402 A1 * | 4/2011 | Oddou ................ A61F 5/0125 602/16 |
| 2012/0053498 A1 | 3/2012 | Horst |
| 2013/0018293 A1 | 1/2013 | Wayd |
| 2013/0178771 A1 * | 7/2013 | Moir ................ A61F 5/0123 602/16 |
| 2013/0245524 A1 | 9/2013 | Schofield |

OTHER PUBLICATIONS

U.S. Appl. No. 61/869,235, filed Aug. 23, 2013, Pending.
U.S. Appl. No. 29/441,832, filed Jan. 10, 2013, Pending.
U.S. Appl. No. 29/441,264, filed Jan. 3, 2013, Pending.
Bledsoe Extender Brace Application Instructions CP020193 Rev A 7/02.
CTi OTS Pro Sport Knee Brace website, accessed Oct. 15, 2012, www.phc-online.com/Ossur_Knee_Brace_p/b-239x.htm.

* cited by examiner

MICRO-ADJUSTABLE TELESCOPING ARMS FOR ORTHOPEDIC BRACES

CROSS REFERENCE TO RELATED APPLICATIONS

This application claims the benefit of U.S. Provisional Application No. 61/755,114, filed Jan. 22, 2013, the content of which is incorporated by reference herein in its entirety.

FIELD OF THE INVENTION

The present invention relates to orthopedic braces and more particularly to orthopedic braces with micro-adjustable telescoping arms.

BACKGROUND OF THE INVENTION

There are many forms of orthoses, or devices used externally to modify the structure and/or function of the skeletal and/or neuromuscular systems of the body. For example, there are orthoses that are applied to the neck, to the spine, to the upper limbs, and to the lower limbs. Additionally, there are many different purposes for using orthoses ranging from rehabilitative, to prophylactic. Rehabilitation braces are typically used to limit the movement of the portion of the body following an injury or a surgery.

Certain rehabilitation braces, for example orthopedic knee braces, typically immobilize the leg and/or limit the motion in both the lateral and medial directions. These braces provide a mechanism to reduce the range of motion for a healing limb. The ability to limit flexion and extension are important features for an effective orthopedic knee brace. To maximize the benefits of an orthopedic brace it must be properly fitted and adjusted to the patient. Adjustment variables include fitting patients of various sizes and body proportions, and accommodating a variety of possible surgical sites. The adjustment of the brace will also be continual as the patient heals and can tolerate larger ranges of motion, as swelling is reduced, and the like. At times there may also be readjustment of the braces paddles to adapt accessories and product upgrades.

To accomplish adjustability in existing orthotic braces, some brace designs utilize a system of holes in the strut. For example, in U.S. Pat. No. 6,821,261 a series of holes incorporated into the brace's strut is disclosed. This system of holes allows support members to be adjusted into a small number of positions on the patient. The holes disclosed in the aforementioned patent slide over a button and a biasing spring forces the button into the respective hole at a particular position. The operator, or physician, must depress the button in order to advance to the next available hole. This is done repeatedly until the closest available length is achieved. One problem with this method is that the notched holes where the locking feature, or button, can engage are grossly separated along the strut, and thus, only provide for gross adjustment of the lengths of the orthopedic brace. In the case of a knee brace, there would be a need to adjust both the upper and lower lengths of the brace (as described in reference to the hinge element). Other orthopedic braces may have additional areas where the length needs to be adjusted, further compounding the gross adjustment issue.

Similarly, in U.S. Pat. No. 7,384,406 B2, a series of notches incorporated into the brace's strut is disclosed. This system of notches, just as in the previous system, allows support members to be adjusted into a small number of positions on the patient. The notches disclosed in this system are engaged by a screw with a biasing spring and a retaining bushing. The biasing spring pushes a button in an upward position. By depressing the same button, the spring pushes the retaining bushing out of a particular notch. With pressure still applied, the length of the portion of the brace is adjusted to the next available notch and the retaining bushing re-engages to lock the length. As previously described, this method only allows for gross adjustment with constant user input and thus accurate size and fit are sacrificed to the detriment of the patient.

Another existing adjustment method utilizes a cam lever and a friction lock to adjust the length of the struts. When the cam lever is unlocked the support members freely move along the struts. This system allows for a range of adjustments and sizing. However, there is no way to index the components into position and as such, accurate adjusting, or re-adjusting, of the length of the portion of the brace is difficult to accomplish.

One aspect of the present invention is an adjustable orthopedic strut system that combines a locking system with an incremental or "micro" adjustment method that is size adaptable and easy to use. One embodiment of the present invention comprises a locking system, adjustable support members, struts, and an indented molded track. The present invention improves user fitting and sizing creating better support and comfort. The present invention provides "micro" incremental adjustments on support members to allow strategic positioning of the support members near surgical incisions without the need for constant user input. Furthermore, the present invention locks and telescopes on a non-interrupted strut surface with minimal "snag" points thus reducing the difficulty in achieving fine adjustments. The system of the present invention easily indicates and indexes in a molded track and can be reduced in scale to fit many orthopedic devices to provide accurate micro-adjustments to a variety of applications and patients.

SUMMARY OF THE INVENTION

The present invention is a system comprising an orthotic brace with at least one hinge; a plurality of deformable struts comprising an indexable, micro-adjustable track, wherein the struts have a first end and a second end, and the first end of the strut is attached to the hinge; a plurality of innermost support members slidably attached to the struts wherein each innermost support member comprises a button, wherein the button is configured to engage the track, such that the support members may be incrementally indexed along the strut and locked when the support member is in the desired position along the track; and a plurality of outermost support members slidably attached to the second end of the struts wherein each outermost support member comprises a button, wherein the button is configured to engage the track, such that the support members may be incrementally indexed along the strut and locked when the support member is in the desired position along the track, thereby locking the outermost support member in position along the track and extend the apparent length of the strut.

In one embodiment of the present invention, the micro-adjustable track comprises a plurality of grooves wherein the plurality of grooves represent increments of adjustment. The increments may be the same along the length of the micro-adjustable track or vary along the length of the micro-adjustable track.

In one embodiment of the present invention, the increments are less than ⅓ of an inch apart. In another embodiment, the increments range from one quarter of an inch increments to one eighth of an inch increments on the same track.

In one embodiment of the present invention, the indexable, micro-adjustable track is flexible. In another embodiment, the indexable, micro-adjustable track is integral to the strut.

In one embodiment of the present invention, the struts are configured to be bent to properly fit a patient.

These aspects of the invention are not meant to be exclusive and other features, aspects, and advantages of the present invention will be readily apparent to those of ordinary skill in the art when read in conjunction with the following description, appended claims, and accompanying drawings.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

In one embodiment of the present invention, the orthotic brace is a knee brace. In certain embodiments, the orthotic knee brace comprises a "micro-adjustable" telescoping system comprising two bendable, lightweight struts or arms extending off an adjustable hinge located axially near the knee. In certain embodiments, one strut extends and telescopes up along the thigh and the other strut extends down the leg along the calf. In one embodiment of the present invention, a series of tubular "telescoping" support members are located along these struts. These support members, when unlocked, are adjustable incrementally along a molded track. In certain embodiments, each of the support members has a strap running radially through it and adjustably connects around the body. The telescoping support members allow the brace to be fit to a variety of patients in specific locations along the leg.

In the current invention the strut or arms are connected to a rotatable hinge mechanism. This hinge mechanism is adjustable in both directions of flexion and extension, allowing the user incrementally to control the user's range of motion. However, it is not outside of the scope of this invention to use other hinge variations. Even attaching the upper and lower struts together in a simple rotatable fashion could suffice in certain applications. In relationship to the struts, the telescoping support members are connected to contoured paddles and allow the brace to be affixed to the user's body. The support member and paddle travel together along the bendable struts and are adjustable along, the length of the limb. These support members are mechanically locked in place once they have been fitted and adjusted to the correct orientation. The current invention's locking mechanism uses a slidable bezel and button configuration. This is not a permanent locking mechanism because support members may have to be readjusted based on the patient's healing patterns (and/or therapy). Once in place they are affixed to the user's body and secured with adjustable straps and closures.

Figure 1A:
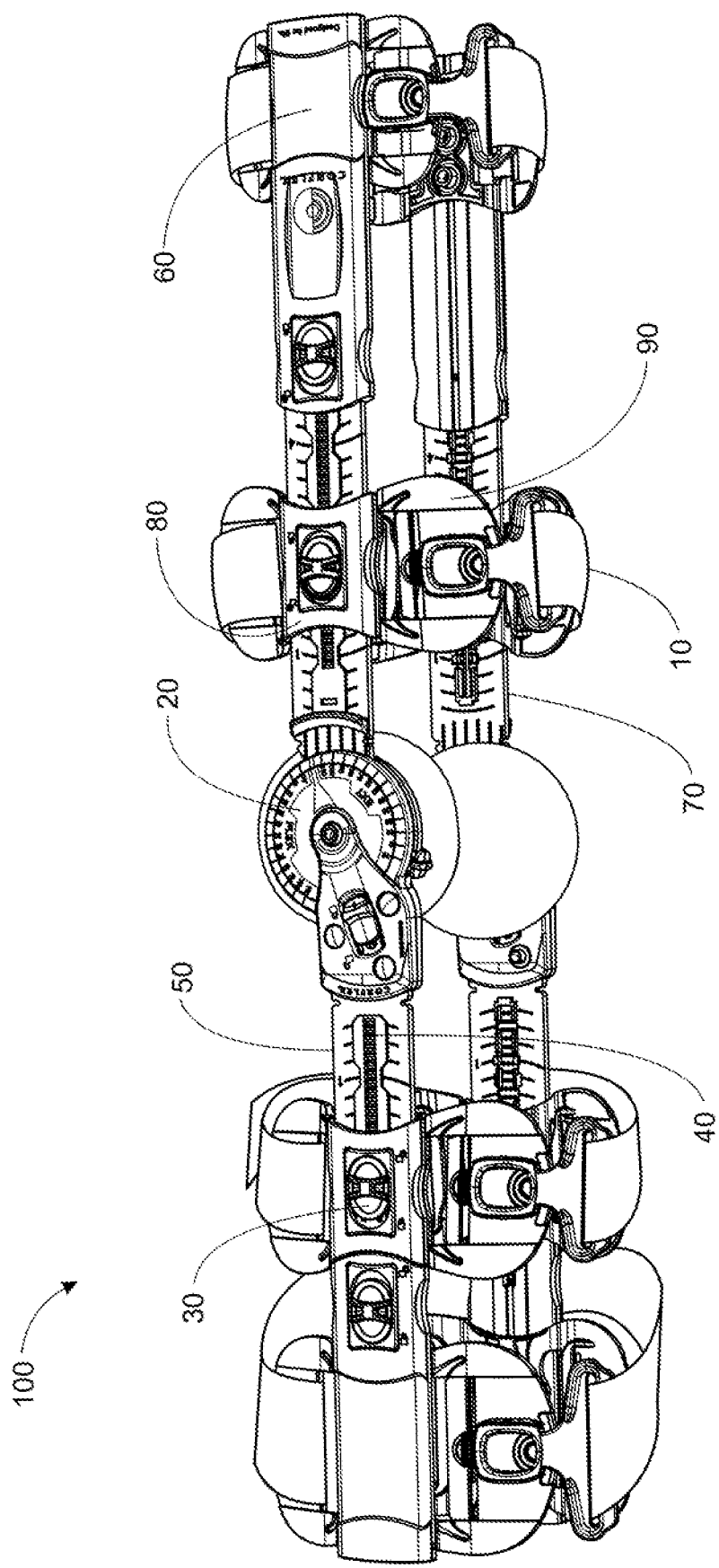
FIG. 1A shows a side view of an entire orthotic knee brace with micro-adjustable telescoping arms of one embodiment of the present invention.

Referring to FIG. 1A, one embodiment of a brace of the present invention is shown. More specifically, an orthotic knee brace of the present invention comprises a brace 100 with innermost 80 and outermost 60 telescoping support members located on a strut 70. The innermost 80 and outermost 60 telescoping support members have padded straps 10 that reversibly connect the brace to the patient. In one embodiment of the present invention, the strut 70 has a molded micro-adjustable track 40 embedded in the strut 70. The flexible, indexable micro-adjustable track is configured to remain integral to the strut when the strut is bent to fit a user so that the adjustment mechanism functions smoothly. An adjustable, locking hinge 20 separates the upper and lower portions of the orthotic knee brace of one embodiment of the preset invention. Easy to use, locking buttons 30 engage the track and hold the support members in place. The outermost support members 60 move along the strut, but also effectively lengthen the brace 100. The innermost support members 80 allow for greater accuracy and flexibly in fitting the brace 100 to a particular patient. The buttons 30 are configured to be unlocked and have the support members slidably indexed along the length of the strut. Once the desired length has been achieved, the button can be locked into position.

Figure 1B:
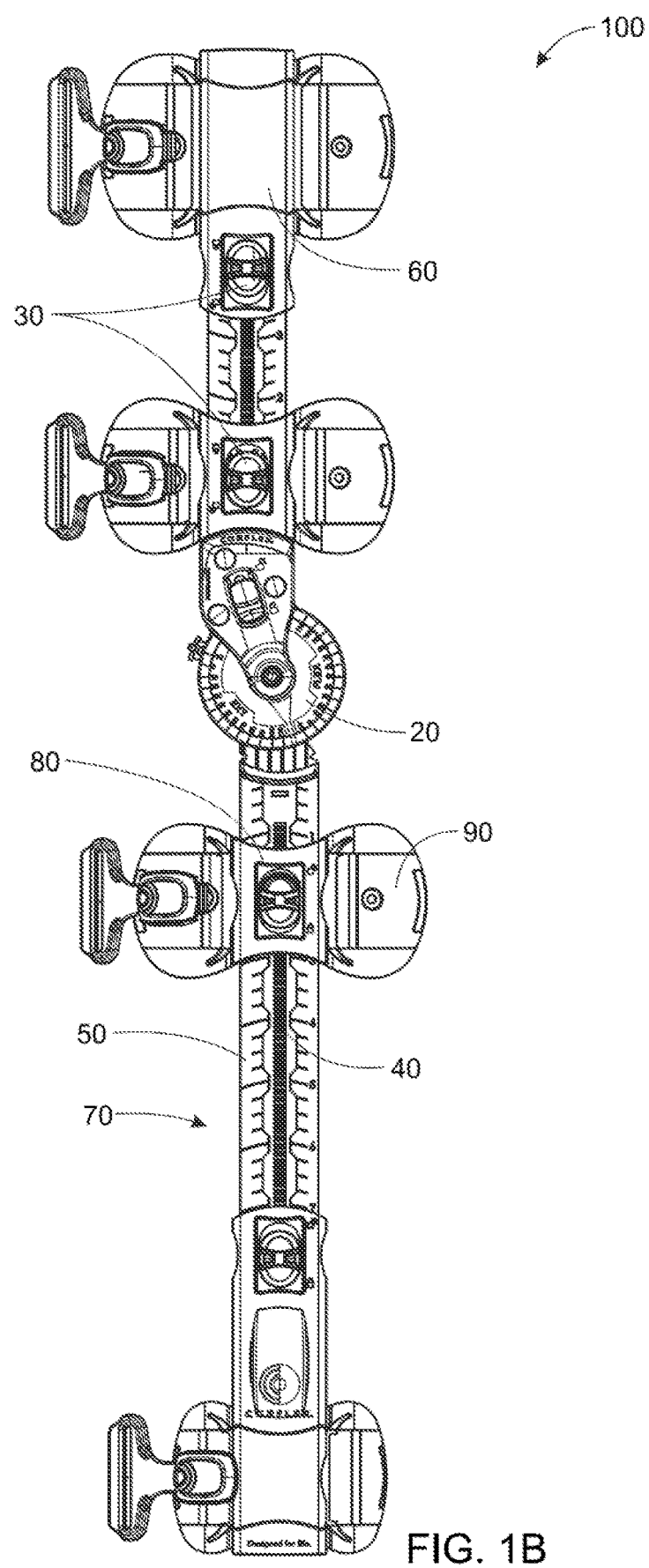
FIG. 1B shows a side view of an orthotic knee brace with micro-adjustable telescoping arms of one embodiment of the present invention.

Referring to FIG. 1B, a side view of one embodiment of an orthotic knee brace of the present invention with micro-adjustable telescoping arms is shown. More specifically, a brace 100 is shown with four moveable support members. The inner most support members 80 travel along a track 40 in the strut 70. An indexed portion 50 provides for accurately reproducible adjustments for the support members. The outermost support members 60 also travel along a track 40 in the strut 70. An indexed portion 50 provides for accurately reproducible adjustments for the support members. The support members contain paddles 90 that support and direct flexible, adjustable straps (not shown) which reversibly attach the brace to a patient. The hinge provides an adjustable, locking mechanism to control the range of motion for both flexion and extension. Locking buttons 30 are located on the tubular support members and engage the track to provide easy to use, micro-adjustability for each support member. Each support member has the ability to be readjusted repetitively to fit the brace to the patient as needed.

Figure 2:
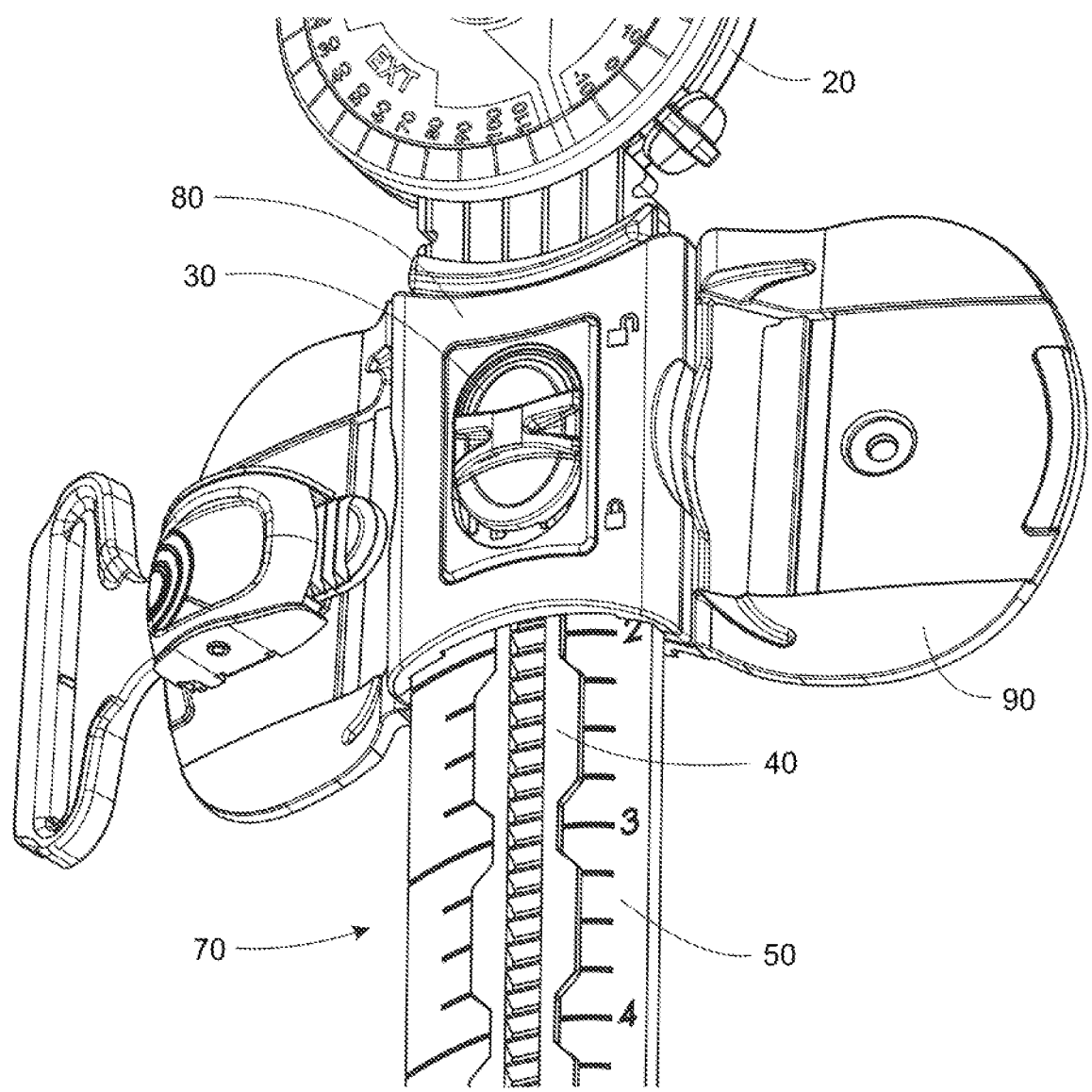
FIG. 2 shows an enlarged view of the micro-adjustable telescoping arm of one embodiment of the present invention.

Referring to FIG. 2, an enlarged view of the micro-adjustable telescoping arm of one embodiment of the present invention is shown. More specifically, FIG. 2 shows one embodiment of the telescoping support member 80, which rides over and along the strut 70. The support member indexes the micro-adjustment using the gradations along the arm 50. The support member comprises an easy to use, easy to lock/unlock button 30, which engages the micro-adjustable track 40. Semi-flexible paddles 90 are carried on the support members and position and hold flexible straps (not shown), which reversibly attach the brace to a patient.

Figure 3:
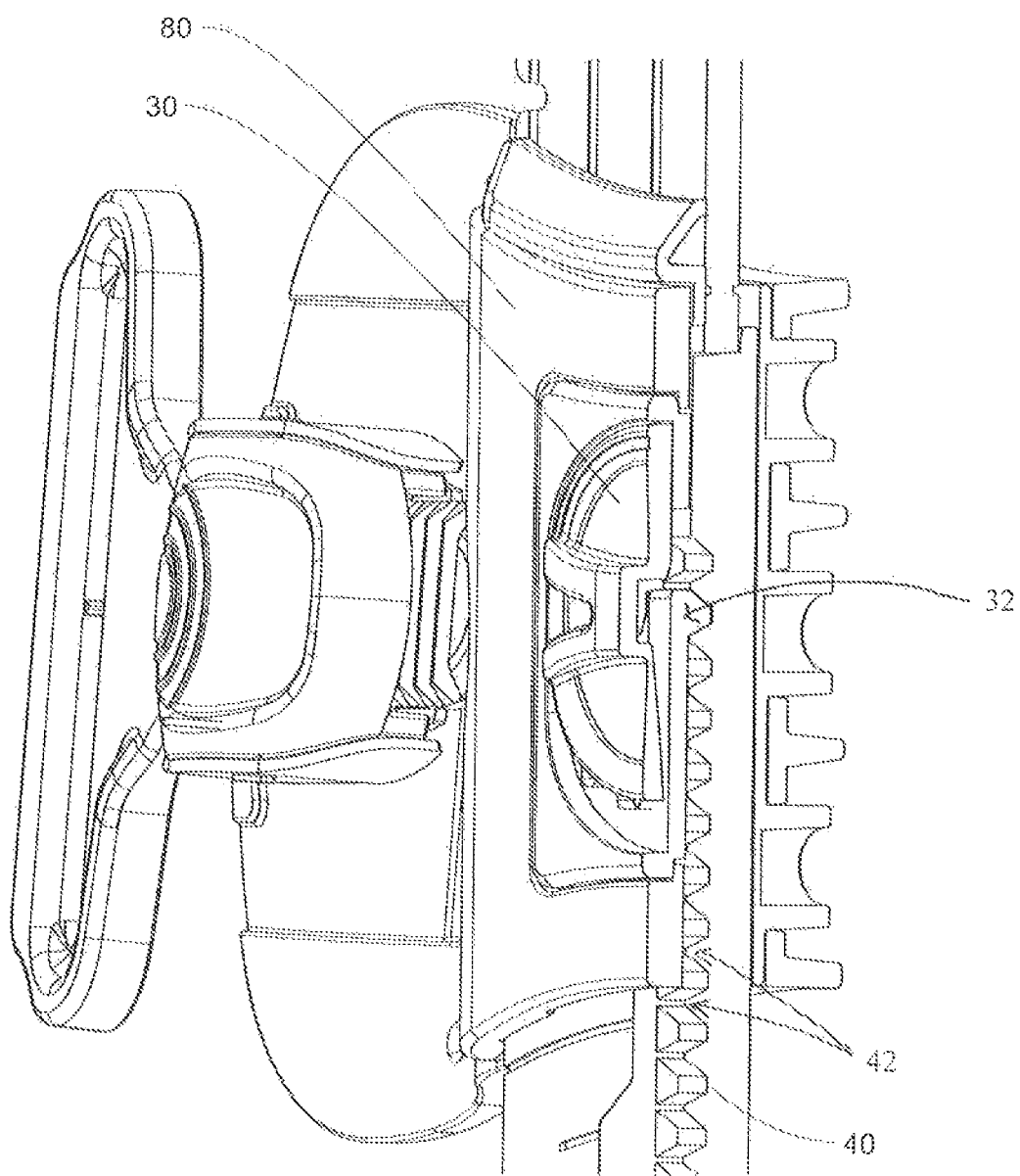
FIG. 3 shows a cross sectional view of the micro-adjustable telescoping arm of one embodiment of the present invention.

Referring to FIG. 3, a cross sectional view of the micro-adjustable telescoping arm of one embodiment of the present invention is shown. More specifically, FIG. 3 shows one embodiment of the locking button 30 of the present invention. In certain embodiments, the locking button is recessed into a bezel and comprises a locking tooth 32 for engaging a plurality of grooves 42 in the track 40. In another variation, it is possible for the locking feature to be part of the telescope and the locking button can vary in motion, such as a rotation or lever instead of a slide. Conversely, a containing pin can be used instead of a locking arm and pressed down into the track by a slide, rotation or lever.

Figures 3, 4:
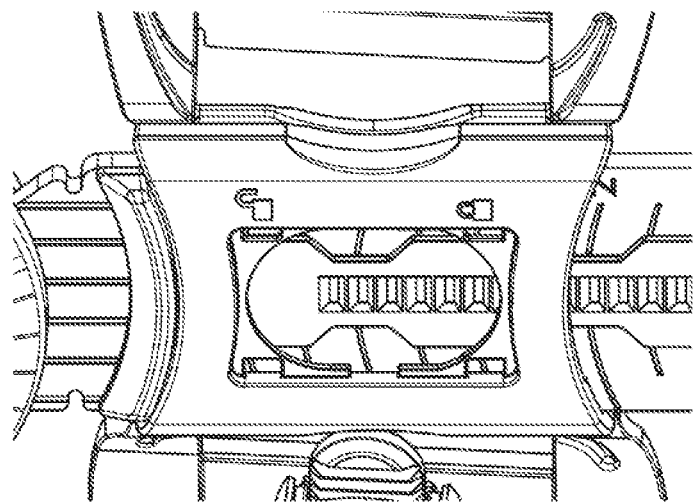
FIG. 4 shows a series of images (4.1-4.6) deconstructing the micro-adjustable telescoping arm of one embodiment of the present invention.
Figures 2, 4:
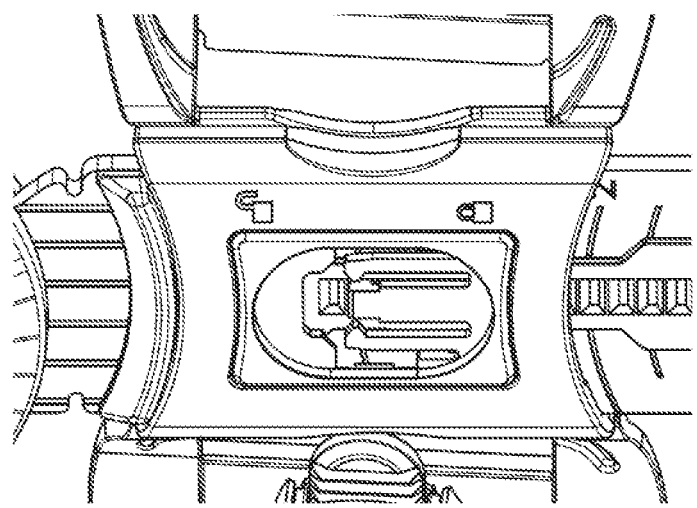
Figures 1, 4:
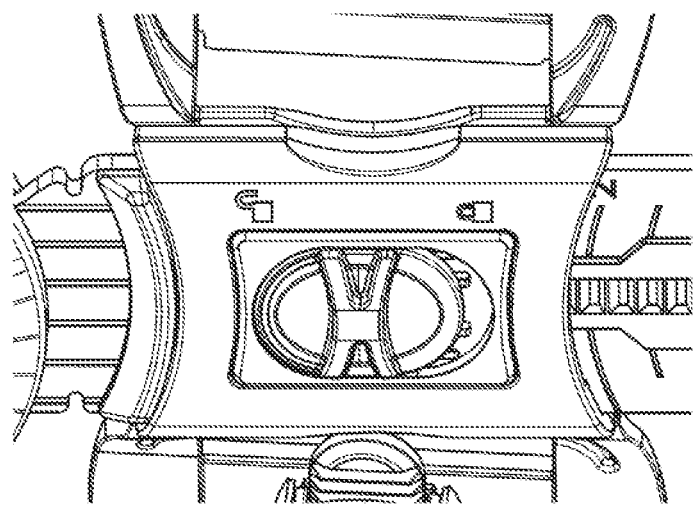
Figures 4, 5, 6:
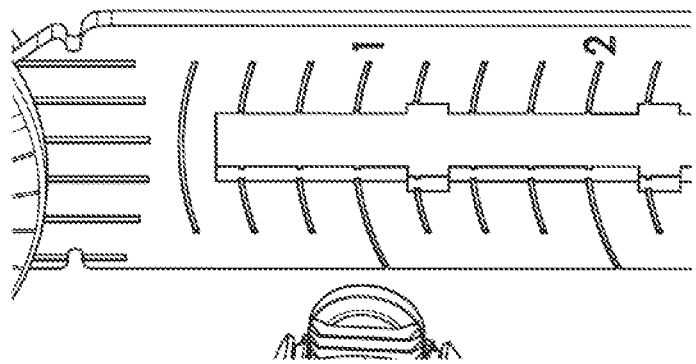
Figures 4, 5:
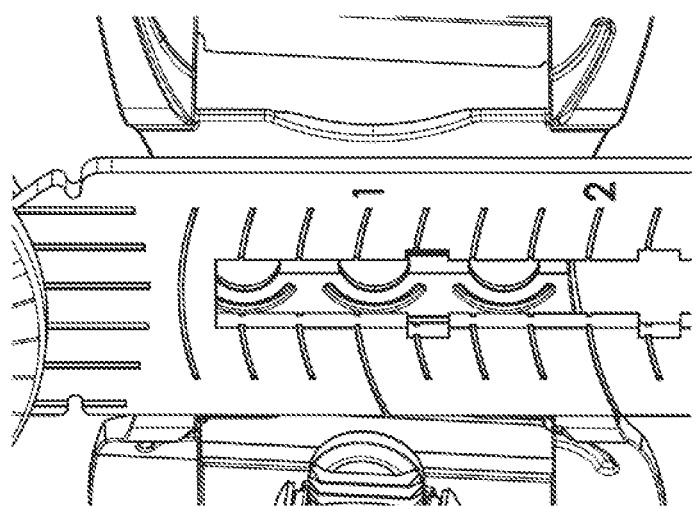
Figure 4:
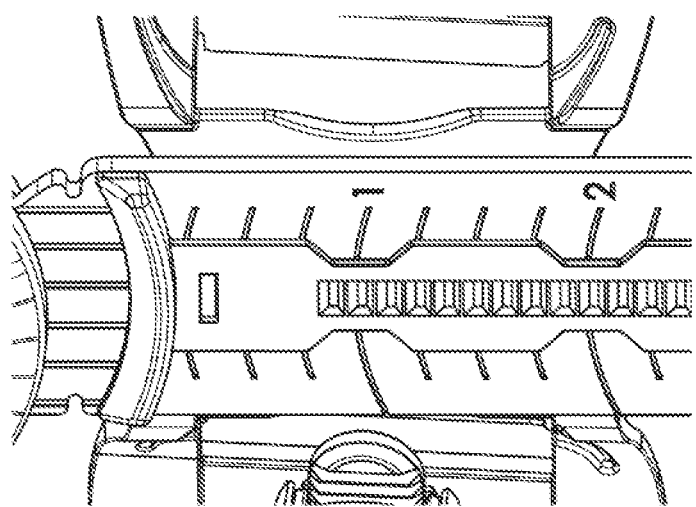

As seen in FIG. 4, one embodiment of the present invention is an orthotic brace with a cut out in the elongated support that incorporates a modular approach to building the brace. This modular approach offers a series of benefits including 1) the molded track can be embedded inside the metal support to create an internal low profile design, 2) the molded track bends more easily with the support than if it were mounted or applied, 3) the molded track can be specifically designed to have the proper locking geometry, 4) the molded track can be changed and incorporated into an existing metal stamping, 5) the separate molded track allows for significant control in material choice, and 6) the separate molded track provides the advantage of being able to change materials without interrupting the design.

Referring to FIG. 4, a series of images (4.1-4.6) deconstructing the micro-adjustable telescoping arm of one embodiment of the present invention is shown. More specifically, in FIG. 4.1 the full assembly of the slidable and lockable plastic button is shown. Plastic material options for all of the following related components include ABS, polypropylene, polyethylene, nylon, polycarbonate and even compounded resins. In FIG. 4.2, the mechanical, snap-fit slidable button is removed to expose the fixed bezel portion with an integrated locking button, which comprises a locking tooth to engage the track. In this assembly, the bezel is snap-fit into position. However, in other configurations it can easily be adhesively bonded or mechanically fastened. In FIG. 4.3, the bezel is removed to expose the portion of the support member, which surrounds the strut. Its tubular design allows it to travel closely along the strut. In FIG. 4.4, the tube portion of the support member is removed to expose the track in the arm. The tubular support member may be mechanically joined to the paddle by means of adhesive, fasteners, snap-fit, sonic welding or even the heat stake process. In FIG. 4.5, the adjustment track is removed to expose the paddle 90 as is interacts with the arm. In FIG. 4.6, the paddle is finally removed to expose the arm.

In one embodiment of the present invention, the struts for the orthotic brace utilize laser or die cut metal. In certain embodiments, the struts utilize 6061 T6 aluminum. This material choice is strong, lightweight, non-corrosive and bendable. However, other sufficient strut material replacements include aluminum alloys 7075 and 5052 for their specific metallurgical properties.

In one embodiment, the adjustable track is molded from an ABS blend and slides into place through a series of snaps and slides. Considering there are many choices of plastics with this approach the material can be reconfigured to create a different result. The product can be made more flexible or rigid depending on the plastics blend and composition. Other viable materials for the track include polypropylene, nylon, polyester, polycarbonate and even compounded resins. Furthermore, since the part is molded, the track can be configured to a variety of shapes and geometries. Results from this include a range of different increments of adjustment.

For example, in certain embodiments, the track is molded to be more adjustable in a specific area allowing the engagement tooth from the locking mechanism to change from eighth of an inch increments to one quarter of an inch increments on the same track. This creates the advantage of fully controlling the micro adjustment of the brace if desired. The flexibility of the micro-adjustable telescoping arms of the present invention allow for orthoses that are easy to adjust and to re-adjust as needed by each particular patient at each particular stage of treatment. The fine adjustments provide a more accurate and secure lit for a large variety of patients who are dealing with a range of different injuries and/or surgeries.

In one embodiment, the adjustable track is adjustable in a range of ⅛" increments. However other possible increments include 3/16" and ¼" if desired and Metric equivalents.

Within the scope of a modular design in one embodiment of the present invention, the ability separately to mold the adjustable track allows for many functional advantages. One benefit of the modular design of one embodiment of the present invention includes having incremental control of the support members around a patient's surgical site or sites. Another benefit of one embodiment of the present invention is the ability to change the increment engagement along the track if fine increments are not needed. Another benefit of one embodiment of the present invention is having certain smooth areas along the track and/or non-locking areas along the track for certain applications.

One embodiment of the brace of the present invention attaches to the patient's leg through a series of straps woven through the support members. To make the brace adjustable (telescoping) the support members must travel up and down the strut assembly. It is, however, essential that the support members move easily along the strut assembly and still maintain the ability to be locked into position. This is in contrast to other patents like U.S. Pat. Nos. 7,385,406 and 6,821,261 that require downward pressure to be constantly applied to the button in order to extend the length of the brace. This makes adjustment, albeit coarse adjustment, tedious and awkward as you travel from one point to the next. It is desirable to have fine adjustments, but also to have smooth adjustments when dealing with an injured patient.

In certain embodiments of the present invention, the support member and locking mechanism are made up of the following: a support member molded as a tubular channel (Lustran or other ABS equivalent) that excepts the bezel and button mechanism; a molded bezel (Lustran or other ABS equivalent) with integrated locking tooth that snaps into the support member; a molded button (Lustran or other ABS equivalent) that snap fits into the bezel located in the support member. The bezel and button assembly is permanently mounted into the support member through a series of interference fits. In certain embodiments, the completed assembly has the ability to be repeatedly locked/unlocked into position. As the brace is being fit in the unlocked position, the locking tooth floats along the incremental track in and out of molded valleys. This allows the person applying the brace not to have to keep his finger on the button until it is ready for final engagement. Once the brace is fully adjusted the support members are then locked into position. If any more "micro-adjustment" is desired, the person simply unlocks the button and continues to fit the brace. This helps in fitting around surgical sites and tender areas by repositioning the supports delicately and with fine degrees of adjustment.

The micro-adjustment system of the present invention is very distinct from prior art in a number of ways. First, U.S. Pat. Nos. 7,383,406 and 6,821,261 telescope by indexing a tensioned button into stamped metal holes. As the holes get too small and incremental, the button/lock becomes more difficult to locate into position. Because of this, the holders of these patents have manufactured their product with one half inch increments. Second, U.S. Pat. No. 3,805,773 uses punched holes in metal and a releasable pin to index the telescoping struts providing only similarly gross adjustments. The micro-adjustable telescoping arms of the present invention offer a novel solution to both problems by having a track with incremental "micro-adjustment" spacing and a hands five corresponding lock/unlock button. These embodiments present the benefits of telescoping "micro-adjusting" support members with an easy to use luck/unlock button.

In another embodiment of the present invention, the orthotic brace may be integrally molded, machined or stamped such that the track and strut is one unit. In certain embodiments, braces can incorporate a single material strut. In certain embodiments, the single material strut can be a knee brace. In certain embodiments, the single material strut can he an elbow brace or T.L.S.O. back brace component. Additionally, the strut can be applied to a brace where the strut is used as a "stay" and does not require a bend. In certain embodiments of the present invention, the strut is comprised of lightweight composites, molded plastics, extruded plastics, and the like.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed:

1. An orthotic brace, comprising:
   at least one hinge;
   a plurality of deformable struts comprising an indexable, micro-adjustable track, wherein the indexable, micro-adjustable track has a length and comprises a plurality of grooves wherein the plurality of grooves represent increments of adjustment and wherein each of the struts have a first end and a second end and a length, the first end of each of the struts is attached to the hinge;
   a plurality of innermost support members slidably attached to each of the struts at the first end wherein each innermost support member comprises a button, wherein the button is configured to releasably engage the indexable, micro-adjustable track by engaging a locking tooth with one of the plurality of grooves, such that each of the innermost support members may be incrementally indexed along the length of the strut and locked in position when each of the innermost support members is in a desired position along the length of the indexable, micro-adjustable track; and
   a plurality of outermost support members slidably attached to the second end of each of the struts wherein each outermost support member comprises a button, wherein the button is configured to engage the indexable, micro-adjustable track by engaging a locking tooth with one of the plurality of grooves, such that each of the outermost support members may be incrementally indexed along the length of the strut and locked in position when each of the outermost support members is in a desired position along the indexable, micro-adjustable track,
   thereby locking each of the outermost support members in position along the indexable, micro-adjustable track extending the apparent length of the strut.

2. The orthotic brace of claim 1, wherein the increments of adjustment are the same along the length of the micro-adjustable track.

3. The orthotic brace of claim 2, wherein the increments of adjustment are less than ⅓ of an inch apart.

4. The orthotic brace of claim 1, wherein the increments of adjustment vary along the length of the micro-adjustable track.

5. The orthotic brace of claim 4, wherein the increments of adjustment range from one quarter of an inch increments of adjustment to one eighth of an inch increments of adjustment on a single track.

6. The orthotic brace of claim 1, wherein the indexable, micro-adjustable track is flexible.

7. The orthotic brace of claim 1, wherein the indexable, micro-adjustable track is integral to the strut.

8. The orthotic brace of claim 1, wherein the struts are configured to be bent to fit a patient.

9. An orthotic brace, comprising:
   a first deformable strut having a first end, a second end, and a length, wherein the first deformable strut comprises a first indexable, micro-adjustable track comprising a plurality of grooves that represent increments of adjustment;
   a second deformable strut having a first end, a second end, and a length, wherein the second deformable strut comprises a second indexable, micro-adjustable track comprising a plurality of grooves that represent increments of adjustment;
   a hinge connecting the first end of the first deformable strut with the first end of the second deformable strut;
   a first support member slidably attached to each of the first and the second deformable struts at the first end of the respective struts; and
   a second support member slidably attached to each of the first and the second deformable struts at the second end of the respective struts and capable of extending the apparent length of the strut;
   wherein each of the first and the second support members comprises a button configured to releasably engage the indexable, micro-adjustable track by engaging a locking tooth with one of the plurality of grooves, such that each of the first and the second support members may be incrementally indexed along the length of the first or the second deformable strut and locked into position when each of the first and the second support members is in a desired position along the length of the indexable, micro-adjustable track.

* * * * *